United States Patent
Ho et al.

(10) Patent No.: US 11,371,001 B2
(45) Date of Patent: Jun. 28, 2022

(54) CELL SCREENING DEVICE AND CELL SCREENING METHOD

(71) Applicant: SHANGHAI AUREFLUIDICS TECHNOLOGY CO., LTD, Shanghai (CN)

(72) Inventors: Yu-Han Ho, Shanghai (CN); Yimin Guan, Shanghai (CN)

(73) Assignee: SHANGHAI AUREFLUIDICS TECHNOLOGY CO., LTD, Shanghai (CN)

( * ) Notice: Subject to any disclaimer, the term of this patent is extended or adjusted under 35 U.S.C. 154(b) by 440 days.

(21) Appl. No.: 16/481,008

(22) PCT Filed: Nov. 21, 2017

(86) PCT No.: PCT/CN2017/112177
§ 371 (c)(1),
(2) Date: Jul. 25, 2019

(87) PCT Pub. No.: WO2018/121130
PCT Pub. Date: Jul. 5, 2018

(65) Prior Publication Data
US 2019/0390148 A1    Dec. 26, 2019

(30) Foreign Application Priority Data

Dec. 29, 2016 (CN) .......................... 201611245966.7

(51) Int. Cl.
*C12M 3/06* (2006.01)
*C12M 1/02* (2006.01)
*C12Q 1/04* (2006.01)

(52) U.S. Cl.
CPC ............ *C12M 23/16* (2013.01); *C12M 27/00* (2013.01); *C12Q 1/04* (2013.01)

(58) Field of Classification Search
CPC ..... B01L 2200/0652; B01L 2400/0442; B01L 3/502761; C12M 23/16; C12M 27/00; C12M 47/04; G01N 21/76
See application file for complete search history.

(56) References Cited

U.S. PATENT DOCUMENTS

2011/0003330 A1* 1/2011 Durack ............ B01L 3/502761
435/34
2012/0190104 A1    7/2012 Foster et al.

FOREIGN PATENT DOCUMENTS

CN    1735466 A    2/2006
CN    103586221 A    2/2014
(Continued)

*Primary Examiner* — Jennifer Wecker
*Assistant Examiner* — Jonathan Bortoli
(74) *Attorney, Agent, or Firm* — Novick, Kim & Lee, PLLC; Allen Xue

(57) ABSTRACT

Provided are a cell screening device and a cell screening method, for use in performing screening on different cells. The cell screening device is provided with: at least two flowing channels, used for allowing a solution containing cells to flow through; a communicating path, used for allowing the adjacent flowing channels to communicate with each other; a detection unit, used for detecting the types of cells in the solution flowing in the flowing channels; and a screening actuator, generating push force according to the detection result of the detection unit, so as to push cells in the solution flowing in the flowing channel to flow into the adjacent flowing channel through the communicating path.

11 Claims, 4 Drawing Sheets

(56) References Cited

FOREIGN PATENT DOCUMENTS

| CN | 103998394 A | 8/2014 | |
|---|---|---|---|
| CN | 105008895 A | 10/2015 | |
| WO | WO-2004025266 A2 * | 3/2004 | ......... G01N 15/1459 |
| WO | 2016007635 A1 | 1/2016 | |

* cited by examiner

CELL SCREENING DEVICE AND CELL SCREENING METHOD

This application is a national stage entry of PCT/CN2017/112177 filed on Nov. 21, 2017, which claims the benefit of priority from Chinese Patent Application No. 201611245966.7 filed on Dec. 29, 2016, the entire content of which is incorporated herein by reference in its entirety.

TECHNICAL FIELD

The present application relates to the field of biomedical technology, and in particular, to a cell screening device and a cell screening method.

BACKGROUND

Flow Cetometry is a device for automatic analysis and screening of cells based on the principle, that is, to stain target cells with a specific fluorescent dye against the specific biomarker of the target cells and perform fluorescence detection on each single cell through microchannels to select the target cells and separate them from other cells. Wherein, the specific biomarker may be, for example, a protein or an antibody on cell membranes. FIG. 1 is a schematic illustration of staining a target cell with a fluorescent dye. As shown in FIG. 1, the target cell 100 has a specific bio-marker 101 on its surface, so that a fluorescent dye molecule 102 can combine with it to stain the target cell 100.

FIG. 2 is a schematic illustration of a cell sorting system of conventional way. The existing cell sorting system generally uses an ultrasonic pressure crystal and a high voltage electrostatic field. For example, the ultrasonic pressure crystal device, installed on the cell flow chamber, generates vibration of high frequency while being energized, so that micro droplets 201 are generated in the cell flow chamber 200 and each droplet containing a cell 202 to be detected. The laser 203 irradiates the droplet 201 with laser light. If the fluorescence analyzer 204 detects that the droplet emits fluorescence corresponding to the fluorescent dye, indicating that the cell contains the target biomarker, the liquid droplets are charged so that they can fall to the left or to the right under the traction of the high voltage electrostatic field through the deflecting plate 205 and collected while falling into the target container; otherwise, the cell turns out to be free of the target biomarker, so that it is not to be charged, and the droplet will fall directly to the waste collection in the middle.

It should be noted that the above description of the technical background is only for purposes of facilitating the clear and complete description of the technical solutions of the present application, and facilitating understanding by those skilled in the art. The above technical solutions are not considered to be well known to those skilled in the art simply because these aspects are set forth in the background section of this application.

SUMMARY

The inventors of the present application found that the conventional cell sorting method using charging and electrostatic field, as in an open system, is impossible to carry out sample detection with a need for fully enclosed detection. Moreover, charging droplets containing cells during the sorting process may cause damage to the cells or cause changes inside the cells.

The present application provides a cell screening device and a cell screening method for detecting a cell-containing solution flowing in a flow channel, and pushing cells meeting the requirements into adjacent flow channels, thereby enabling fully enclosed detection of the sample, with less damage to cells and lower cost.

According to an aspect of the present application, a cell screening device for screening different cells is provided, wherein the cell screening device has:

at least two flow channels for flowing through a cell-containing solution;

a communicating path for connection between adjacent ones of the at least two flow channels;

a detection unit for detecting types of the cells in the cell-containing solution flowing in the flow channels;

a screening actuator that generates a driving force according to a detection result of the detection unit to push the cells in the cell-containing solution flowing in the flow channel into an adjacent flow channel via the communicating path.

According to another aspect of the present application, the screening actuator generates bubbles that push cells in the cell-containing solution into the adjacent flow channel via the communicating path.

According to another aspect of the present application, the cell screening device further comprises:

a driver, located at a beginning and/or end of the flow channels for driving the cell-containing solution to flow in the flow channels.

According to another aspect of the embodiments of the present application, the cell screening device further comprises:

a collection unit, located at an end of the flow channels for collecting solutions and cells flowing to the end of the flow channels.

According to another aspect of the present application, the screening actuator and the communicating path are disposed opposite to each other on both sides of the flow channels along a flowing direction of the cell-containing solution.

According to another aspect of the present application, the at least two of the flow channels comprise a first flow channel and a second flow channel, wherein the first flow channel flows through a solution containing at least two types of cells. The detection unit detects the types of cells in the first flow channel. When a first predetermined type of cells is detected, the screening actuator generates a driving force to push the first predetermined type of cells via the communicating path between the first flow channel and the second flow channel into the second flow channel, and other cells beside the first predetermined type continue to flow along the first flow channel.

According to another aspect of the present application, a cell screening method for screening different cells is provided, wherein the cell screening method comprises:

flowing a solution containing various types of cells in a flow channel;

detecting types of the cells in the solution flowing in the flow channel; and pushing the cells in the solution flowing in the flow channel into an adjacent flow channel via a communicating path according to a detection result of the types of the cells.

According to another aspect of the present application, the cell screening method further comprises: driving the solution to flow in the flow channel.

The beneficial effects of the present application comprises: samples can be performed fully enclosed detection, with less damage to cells and lower cost.

Specific embodiments of the present application are disclosed in detail with reference to the following description and appended drawings, indicating the manner in which the principles of the application can be employed. It should be understood that the embodiments of the present application are not limited in scope. The embodiments of the present application comprise many variations, modifications, and equivalents within the scope of the appended claims.

Features described and/or illustrated with respect to one embodiment may be used in one or more other embodiments in the same or similar manner, in combination with, or in place of, features in other embodiments.

It should be emphasized that the term "comprising" or "comprises", when used herein, refers to the presence of a feature, object, step or component, but does not exclude the presence or addition of one or more other features, objects, steps or components.

BRIEF DESCRIPTION OF THE DRAWINGS

The drawings are included to provide a further understanding of the embodiments of the present application, and are intended to illustrate the embodiments of the present application Obviously, the drawings in the following description are only some of the embodiments of the present application, and those skilled in the art can obtain other drawings according to the drawings without any inventive effort. In the drawing.

DETAILED DESCRIPTION OF THE INVENTION

Figure 1:
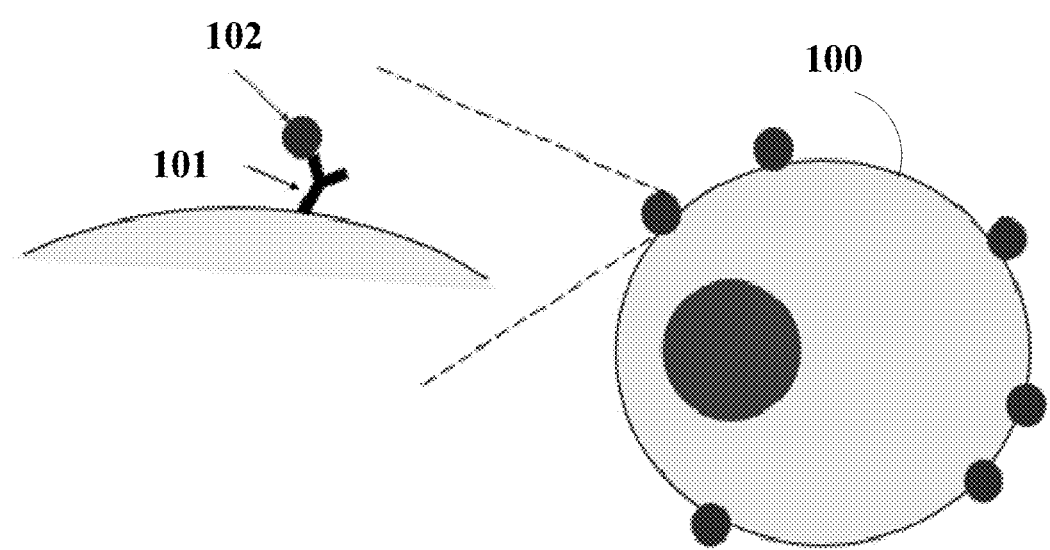
FIG. 1 is a schematic diagram of staining a target cell with a fluorescent dye.
Figure 2:
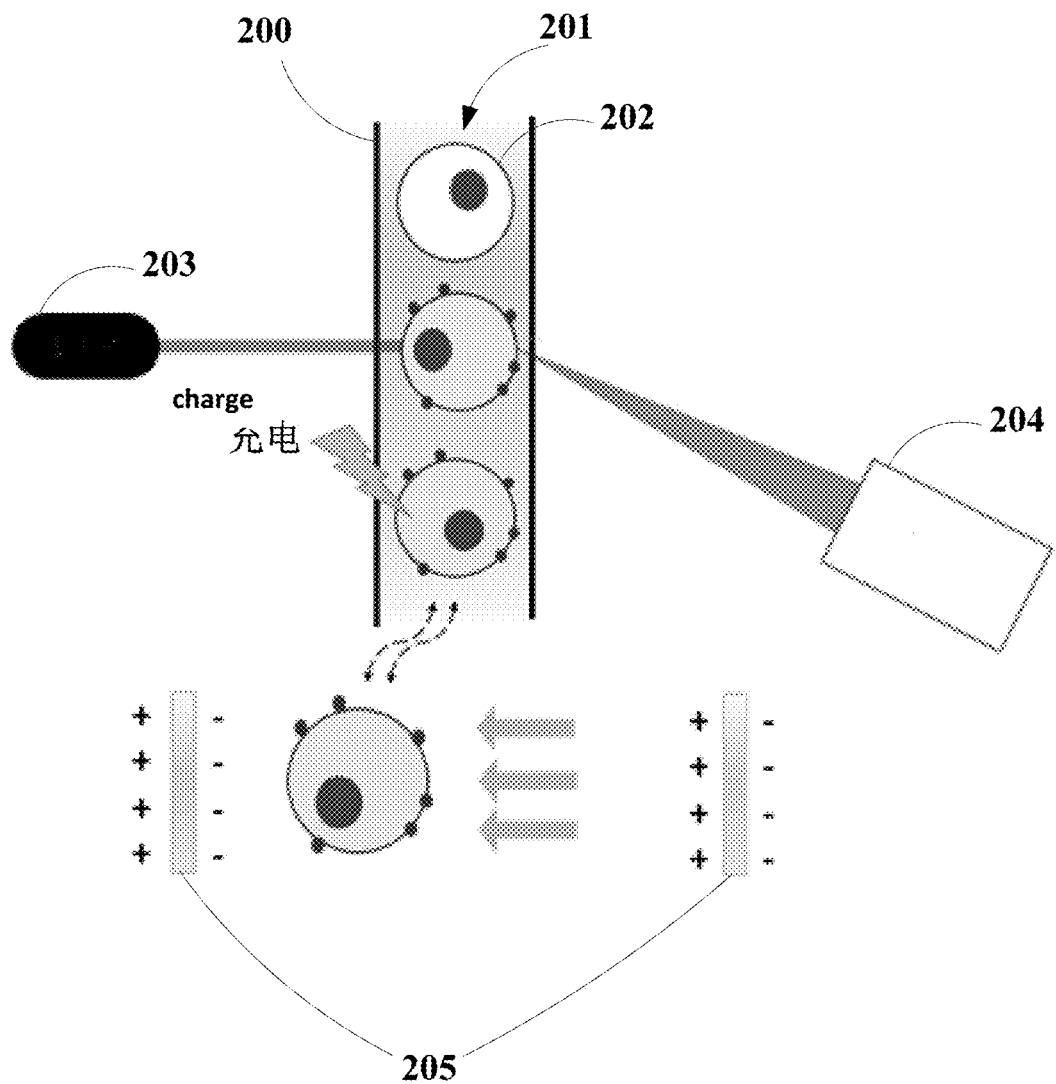
FIG. 2 is a schematic diagram of a cell sorting system of prior art.

The foregoing and other features of the present application will be apparent referring to the drawings and the following specification. The specific embodiments of the present application are specifically disclosed in the specification and the drawings, which illustrate a part of the embodiments in which the principles of the present application may be employed. It should be understood that the present application is not limited to the described embodiments, but instead includes all modifications, variations and equivalents falling within the scope of the appended claims.

Example 1

Example 1 of the present application provides a cell screening device for screening different cells.

Figure 3:
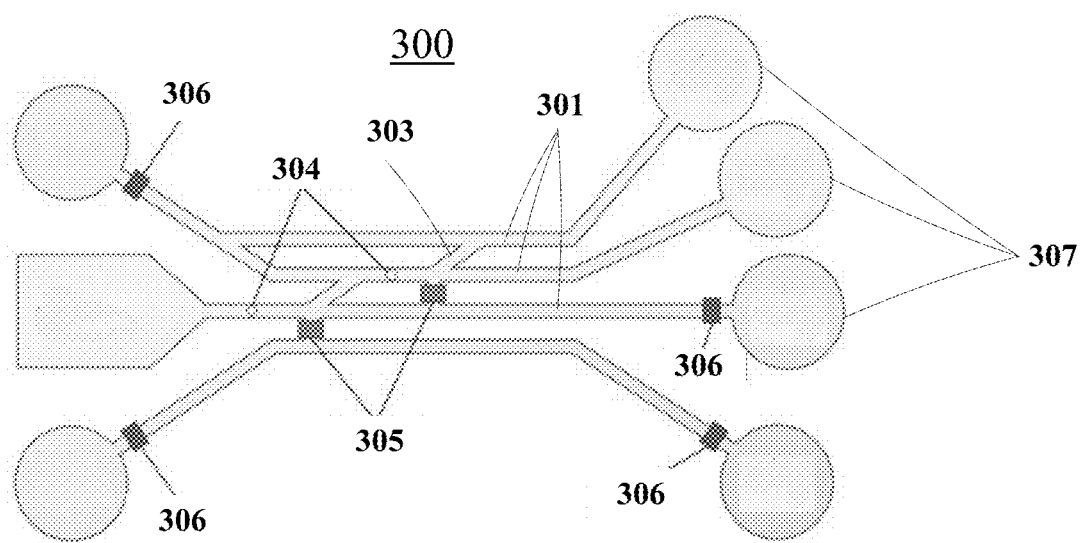
FIG. 3 is a schematic diagram of a cell screening device of an embodiment of the present application.

FIG. 3 is a schematic diagram of the cell screening device 300. As shown in FIG. 3, the cell screening device 300 has at least two flow channels 301, a communicating path 303, a detection unit 304, and a screening actuator 305.

Wherein, the at least two flow channels 301 are used to flow through a solution containing cells; the communicating path 303 is used for communication between adjacent flow channels 301; and the detection unit 304 is used to detect the type of cells in the solution flowing in the flow channel 301.

The screening actuator 305 generates a pushing force according to the detection result of the detection unit 304 to push the cells in the solution flowing in the flow channel 301 into the adjacent flow channel 301 via the communicating path 303.

In the cell screening device of the present example, the cells are in the flow channel or communicating path, so that the cells can be performed fully enclosed screening, without using electric shock or the like, and accordingly with small damage to the cells. Moreover, the conventional deflection device or the like is not required, resulting in low cost.

In this example, the number of flow channels can be determined according to the types of cells to be screened, and the more types to be screened, the more number of flow channels should be. In the present example, the flow channel 301 can be produced using a microelectromechanical system (MEMS) manufacturing process, and a flow section of the flow channel 301 can be tens to hundreds of microns in size, thereby forming a microchannel. Furthermore, a material of the flow channel 301 may be materials commonly used in MEMS technology, such as silicon, silicon oxide or silicon nitride.

In the present example, the communicating path 303 are used to connect adjacent flow channels, so the number of communicating path 303 can be set according to the number of the flow channels. Description related to the size of flow-through section, material and the manufacturing process of the communicating path can be referred to that of the flow channel 301.

In the present example, the detection unit 304 can be used to detect the types of cells in the flow channel 301. For example, the detection unit can be composed of a pair of lasers and a fluorescence detector, and the cells in the solution can be dyed by various fluorescent dyes. Wherein, the laser can irradiate the flow channel 301 with laser light, and the fluorescence detector can detect whether the position irradiated by the laser emits a specific fluorescence, and if a specific fluorescence is emitted, it is indicated that a specific type of cells flow through the position where the laser irradiates. Further, the embodiment is not limited thereto, and other kinds of detection units may be used to detect the type of cells in the solution.

In the present example, the detection unit 304 can also be set according to the number of flow channels. For example, the detection unit can be disposed in the vicinity of the flow channel where the type of the cells needs to be detected.

In the present example, the screening actuator 305 can generate bubbles that can push cells in the solution into the adjacent flow channel 301 via the communicating path 303. For example, the screening actuator 305 can have a heating unit, which can heat the solution to generate bubbles to push cells in the solution into adjacent flow channels.

Figure 4:
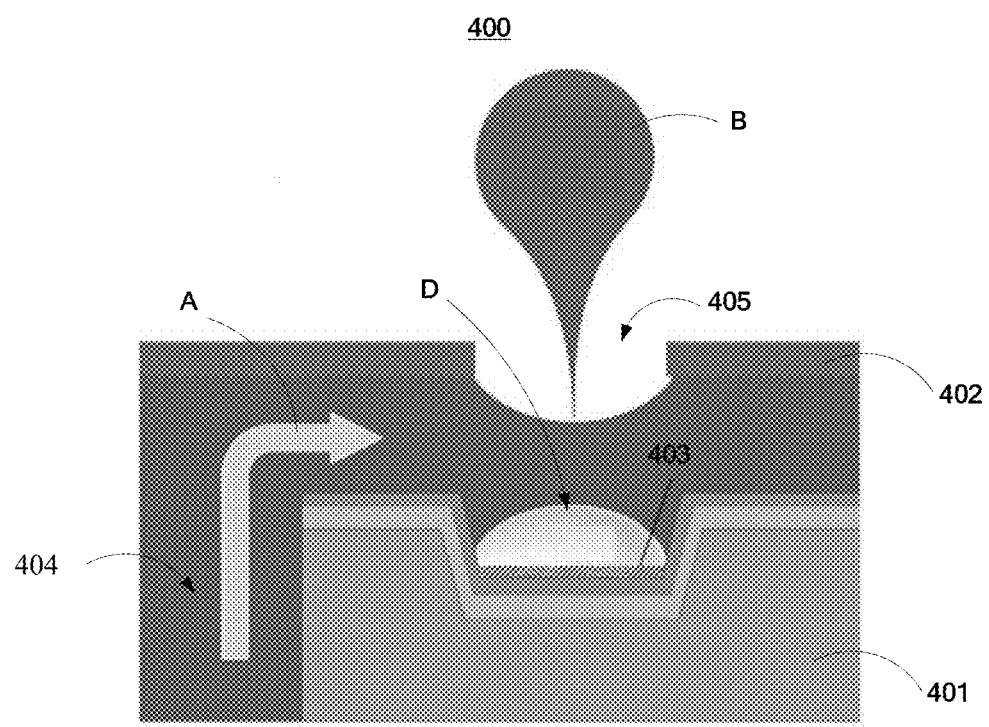
FIG. 4 is a schematic diagram of the hot injection actuator of the present application.

In one embodiment, the screening actuator 305 can be, for example, a hot-injection actuator. FIG. 4 is a schematic diagram of the hot-injection actuator of the present application. As shown in FIG. 4, the hot-injection actuator 400 may comprise a substrate 401, a cover 402, and a heating unit 403, wherein the cover 402 is disposed in a manner to have a gap with the surface of the substrate 401, and a liquid-flow channel 404 is formed between the cover 402 and the surface of the substrate 40; A heating unit 403 is formed on the surface of the substrate 401 for heating the solution flowing in the liquid-flow channel 404. The heating unit 403 heats the solution to generate bubbles D to push the liquid B containing the cells so that it can be ejected from the opening 405, thereby entering the communicating path. In the present embodiment, the opening 405 may communicate with the communication channel 303, and the liquid-flow channel 404 may connect with the flow channel 301. The arrow A in FIG. 4 indicates the flow direction of the liquid in the liquid-flow channel 404.

In the present example, the heating unit 403 may heat the solution in an intermittent heating manner to generate bubbles. For example, each heating for a duration of several microseconds, makes the solution heated to several hundred degrees in a short time to generate bubbles.

In the present example, it may not be limited thereto, and the screening actuator 305 may employ other structures and other actuating principles.

In the present example, as shown in FIG. 3, the cell screening device 300 may further have a driver 306, which may be located at the beginning and/or the end of the flow channel 301 for driving liquid to flow in the flow channel 301. The driver 306 may also have a structure of the hot-injection actuator 400 as shown in FIG. 4, wherein the opening 405 of the hot-injection actuator 400 may be on the downstream side of the liquid flow, so that the heater 400 heats up to generate bubbles and ejects droplets from the opening 405, thereby generating a driving force that drives the flow of the liquid.

In the present example, as shown in FIG. 3, the cell screening device 300 may further have a collecting unit 307 located at the end of the flow channel 301 for collecting the solution and cells flowing to the end of the flow channel.

In the present example, as shown in FIG. 3, the screening actuator 305 and the communicating path 303 are disposed opposite to each other on both sides of the flow channel 301 along the flow direction of the solution, thereby facilitating the screening actuator 305 to push the cells into the communicating path 303.

In the present example, at least two of the flow channels comprise a first flow channel and a second flow channel, and the first flow channel flows through a solution containing at least two types of cells. The detection unit 304 detects the type of cells in the first flow channel. When a first predetermined type of cells is detected, the screening actuator 305 generates a driving force to push the first predetermined type of cells via the communicating path between the first flow channel and the second flow channel into the second flow channel, and other cells beside the first predetermined type continue to flow along the first flow channel.

In order to further classify cells other than the first predetermined type and/or cells of the first predetermined type, more flow channels, more detection units, and more screening actuators can be provided.

Figure 5:
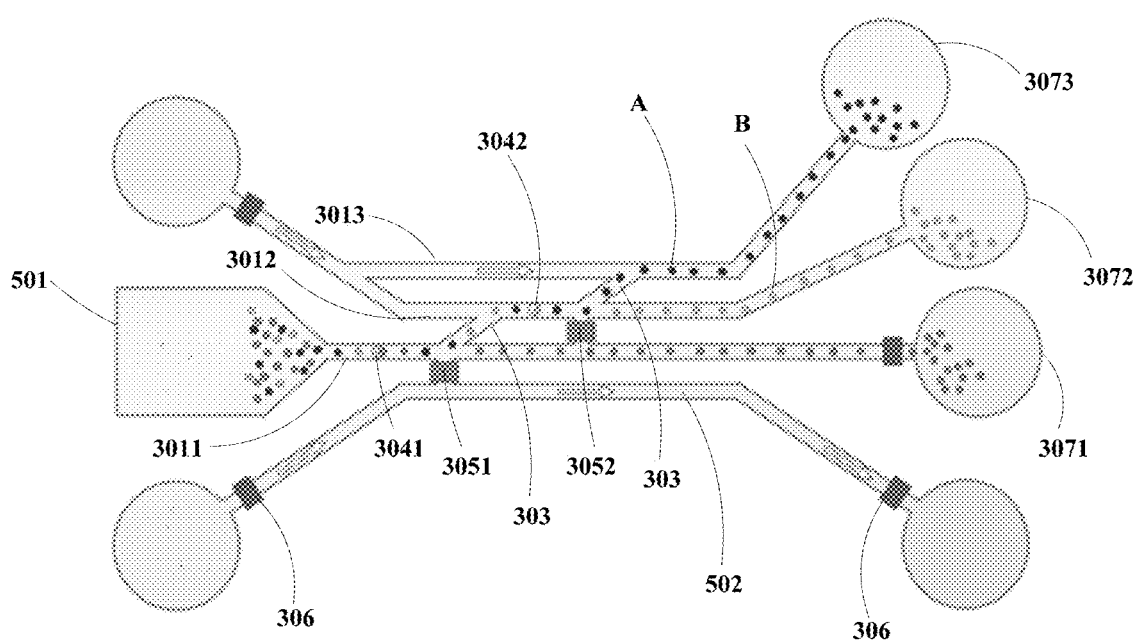
FIG. 5 is a schematic diagram showing cell screening by the cell screening device of an embodiment of the present application.

FIG. 5 is a schematic diagram of the cell screening using the cell screening device of the present embodiment for screening A cells, B cells and normal cells from a sample of mixed cells.

In FIG. 5, the solution sample of mixed cells sufficiently mixed with a fluorescent dye corresponding to the biomarker of A cells and B cells is injected into the first flow channel 3011 at the position 501; When flowing through the first detection unit 3041, it is detected based on the fluorescent signal whether the cell is A cell or B cell or normal cell. For example, when the detection results turn out to be A cell or B cell, A cell or B cell is pushed into the communicating path by the first screening actuator 3051 and enters the adjacent second flow channels 3012. When the detection result of the first detection unit 3041 turn out to be a normal cell, the screening actuator 3051 does not work to generate bubbles when the cell flows through it, so the normal cell enters the first collection unit 3071 along the original flow channel; When the A cells and B cells from the second flow channel 3012 pass through the second detection unit 3042 in the second flow channel 3012, the cell whose detection result is A is pushed into the third flow channel 3013 by the bubbles when passing through the second screening actuator 3052. When the cell with the detection result B flows through the second screening actuator 3052, the second screening actuator 3052 does not work to generate bubbles, so the B cell directly flows into the second collection unit 3072, and the A cell enters the third collection unit 3073 along the third flow channel 3013.

In FIG. 5, the bottommost water flow channel 502 has a driver 306 at the head end and tail end, one for propelling the liquid, and the other one for sucking the generated bubbles away from the channel 502 to avoid blockage.

In FIG. 5, the three cells screened by each of the collection units 3071, 3072, and 3073 can be analyzed in the next step.

According to an embodiment of the present application, a cell screening method is also provided, which performs cell screening using the cell screening device of FIG. 3.

The cell screening method may comprise:
step 601, making a solution containing various types of cells flow in a flow channel;
step 602: detecting types of the cells in the solution flowing in the flow channel; and
step 603, pushing the cell in the solution flowing in the flow channel into the adjacent flow channel via the communicating path according to the detection result of the detection unit.

The method may also comprise driving the solution to flow in the flow channel.

The present invention has been described in connection with the specific embodiments thereof, but it is to be understood that the description is intended to be illustrative and not restrictive. Various modifications and alterations of the present application are possible in light of the spirit and principle of the invention, which are also within the scope of the present application.

The invention claimed is:

1. A cell screening device for screening different cells, comprising:
 at least a first flow channel and a second flow channel passing a cell-containing solution;
 a communicating path connecting the first flow channel and the second flow channel, wherein an inlet of the communication path is open to the first flow channel and an outlet of the communication path is open to the second flow channel;
 a detection unit for detecting types of the cells in the cell-containing solution in the first flow channel; and
 a screening actuator configured to generate a driving force according to a detection result of the detection unit, and configured to push the detected cells in a portion of the cell-containing solution flowing in the first flow channel into the second flow channel via the communicating path,
 wherein the screening actuator comprises an outlet and a heater disposed about the outlet to heat a liquid in the screening actuator, and the outlet of the screening actuator and the inlet of the communicating path are disposed opposite to each other in a width direction of the first flow channel.

2. The cell screening device according to claim 1, wherein the screening actuator generates bubbles that exit the outlet of the screen actuator and push the portion of the cell-containing solution to enter the inlet of the communicating path and to exit from the outlet of the communicating path into the second flow channel.

3. The cell screening device according to claim 1, further comprising:
a first driver located about an inlet of the first flow channel to provide a driving force to drive the cell-containing solution to flow in the first flow channel.

4. The cell screening device of claim 1, wherein the cell screening device further comprises:
a first collection unit connected to an outlet of the first flow channel; and
a second collection unit connected to an outlet of the second flow channel.

5. The cell screening device of claim 1, wherein the screening actuator further comprises a liquid-flow channel connecting the outlet of the screening actuator to a second liquid source.

6. The cell screening device of claim 1, further comprising one or more flow channels, and one or more communicating paths, wherein at least one of the one or more flow channels is connected to the first flow channel or the second flow channel via one of the one or more communicating paths.

7. A cell screening method for screening different cells using the cell screening device of claim 1, comprising:
flowing a solution containing at least a first type and a second type of cells in the first flow channel;
detecting the first and the second types of the cells in the solution flowing in the first flow channel; and
pushing the first type of cells in the solution flowing in the first flow channel into the second flow channel via the communicating path.

8. The cell screening method according to claim 7, wherein the first type of cells in the solution are pushed into the second flow channel via the communicating path by a driving force provided by bubbles generated by the screen actuator.

9. The cell screening method according to claim 7, wherein the cell screening method further comprises: driving the solution to flow in the first flow channel.

10. The cell screening device according to claim 1, further comprising:
a second driver located about an outlet of the first flow channel to provide a driving force to drive the cell-containing solution to flow in the first flow channel.

11. The cell screening device according to claim 1, further comprising:
a third driver located about an inlet of the second flow channel to provide a driving force to drive the cell-containing solution to flow in the second flow channel.

* * * * *